United States Patent

Saadatmanesh et al.

Patent Number: 5,387,211
Date of Patent: Feb. 7, 1995

[54] MULTI-HEAD LASER ASSEMBLY

[75] Inventors: Vahid Saadatmanesh, Irvine; Marvin P. Loeb, Huntington Beach, both of Calif.

[73] Assignee: Trimedyne, Inc., Irvine, Calif.

[21] Appl. No.: 28,839

[22] Filed: Mar. 10, 1993

[51] Int. Cl.$^6$ .............................................. A61N 3/00
[52] U.S. Cl. .................................. 606/10; 606/12; 606/17; 607/89
[58] Field of Search .......................... 606/10–12, 606/17, 18; 607/88, 89; 359/196, 204, 212, 216, 220; 372/10, 15, 17, 23

[56] References Cited

U.S. PATENT DOCUMENTS

| 3,710,798 | 1/1973 | Bredemeier | 606/11 |
|---|---|---|---|
| 4,408,602 | 10/1983 | Nakajima | 606/10 |
| 4,454,882 | 6/1984 | Takano | 606/11 |
| 4,503,854 | 3/1985 | Jako | 606/11 |
| 4,520,816 | 6/1985 | Schachar et al. | 606/18 |
| 5,084,881 | 1/1992 | Farries et al. | 372/6 |
| 5,139,494 | 8/1992 | Freiberg | 606/10 |

Primary Examiner—Stephen C. Pellegrino
Assistant Examiner—Michael Peffley
Attorney, Agent, or Firm—Olson & Hierl, Ltd.

[57] ABSTRACT

A laser device is provided for the co-axial positioning of plural laser beams of same or different wavelengths along a single axis. At least two laser oscillators are provided, each producing a laser beam. A rotary reflector is positioned for intercepting at least one of the produced laser beams and directing the intercepted laser beam separately from, but along a single axis defined by another laser beam.

19 Claims, 6 Drawing Sheets

MULTI-HEAD LASER ASSEMBLY

TECHNICAL FIELD

The present invention relates to devices and procedures for the controlled delivery of laser energy along a selected axis to a target or site. The present invention is especially suitable for use in a medical device for treating a site on the surface of, or inside, a patient's body, as well as for industrial applications.

BACKGROUND OF THE INVENTION AND TECHNICAL PROBLEMS POSED BY THE PRIOR ART

Various systems have been developed or proposed for utilizing laser beam energy for cutting, welding, engraving, etc. Surgical laser devices have also been developed for delivering laser energy from a laser to a site on or in a patient's body. In some applications, these surgical laser devices deliver laser radiation through a flexible, optical fiber from a laser to a target tissue.

Laser energy may be employed to produce a desired effect on tissue, including various types of human tissue. For example, laser energy may be employed to denature proteinaceous components and to cauterize, ablate, or cut tissue.

Typically, effects of a laser beam on human tissue (e.g., ablation, thermo-coagulation, denaturization, cutting, and the like) can be produced with pulses of laser radiation having, for example, at a wavelength of 2,100 nm, an energy density of about 300 mJ/mm² incident on the target site tissue. The effects on the tissue are, of course, dependent upon the amount of incident radiant energy that is absorbed by the tissue and on the absorption efficiency of the employed wavelength. Relatively hard tissues, such as calcified atherosclerotic plaque or bone, require relatively high energy levels for ablation to be effective. Likewise, relatively high average power is needed for ablating a cancerous tumor, for ablation of cartilage in arthroscopy, or like medical procedures where relatively large amounts or relatively hard tissue is to be removed. At a wavelength of 2,100 nm, for example, this would require a power delivery of 40 to 130 watts to the tissue (about 50 to 150 watts at the laser head).

In a variety of surgical procedures involving the cutting of tissue with a laser beam, it is desirable to cut the tissue relatively quickly. In order to cut certain types of tissues at a relatively high rate, the incident laser energy at the tissue site, at a wavelength of 2,100 nm, for example, should preferably be delivered in pulses having a duration of about 200 to 600 microseconds at a repetition rate of 5 to 60 Hertz.

With many types of commercially available laser devices suitable for tissue cutting in medical applications, the production of such high energy levels, or such rapid pulse repetition rates, with a single laser resonator or oscillator (i.e., flash lamp, cavity, and crystal) is difficult or impossible, especially with an excimer, a holmium:YAG, erbium:YAG, ruby, alexandrite or similar lasers having limited output energy level and repetition rate capability. Indeed, many of the commercially available laser devices that are suitable for tissue cutting cannot be operated for extended time periods at such high energy levels or such repetition rates without creating excessive heat or placing excessive stress on the laser device or optical fiber waveguide, which can lead to premature component failure.

Accordingly, it would be desirable to provide an improved system for employing suitable, commercially available laser devices for generating radiant energy at higher energy levels, longer pulse widths, or faster repetition rates for delivery to a tissue site. It would also be advantageous to provide an improved laser system that can accommodate plural laser heads or laser devices for delivering laser energy of different wavelengths in intermittent, or substantially continuous, joined pulses.

Preferably, such an improved system should accommodate the use of commercially available, pulsed or continuous laser devices of the following types: neodymium:yttrium aluminum garnet (Nd:YAG), erbium:yttrium aluminum garnet (Er:YAG), holmium:yttrium aluminum garnet (Ho:YAG), ruby, alexandrite, carbon dioxide, excimer lasers such as argon fluoride (ArF), xenon chloride (XeCl), and other pulsed lasers.

Such an improved system should preferably operate to subject the tissue to pulses of laser energy at a sufficiently high average power and/or repetition rate within a relatively short time span so as to produce the desired effect in the tissue. In particular, it would be desirable to raise the temperature of the tissue to a desired elevated level, notwithstanding the tendency of the tissue temperature to decay or drop over time. In this regard, it will be appreciated that the temperature of tissue that has been initially raised to an elevated temperature $T_o$ decreases approximately according to the following equation:

$$T_t = T_o e^{-t/k}$$

where $T_o$ is the maximum elevated temperature to which the tissue has been raised by a preceding pulse, e is the natural logarithm base, t is any selected time period following the establishment of the temperature $T_o$, k is the tissue thermal diffusion time constant, and $T_t$ is the resulting time-dependent temperature at the end of the time period t.

When tissue is subjected to an initial pulse of laser energy, the tissue temperature rises to a maximum temperature $T_o$, and then the tissue temperature begins to decrease. As the tissue temperature is initially rising, it would be desirable to provide increased energy to the tissue. It is believed that the efficiency of the laser ablation by the tissue can be increased by subjecting the tissue to pulses of laser energy in a way that results in little or no time temperature decay between laser energy pulses. Accordingly, the time span between pulses should be relatively short, preferably much shorter than the tissue thermal diffusion time constant.

For example, when a target site of a typical tissue is elevated to an initial temperature of about 100° C., the tissue temperature decays to about 97° C. in 5 milliseconds, and it would be desirable to subject the tissue to a plurality of laser energy pulses within such a time period or within an even shorter time. Preferably, an improved system should accommodate the emission of energy pulses from two or more conventional, medical lasers within such a time period wherein the laser energy pulses have a typical temporal separation of less than 5 milliseconds—and a pulse width of about 200 to 600 microseconds. The pulse width may vary depending upon a specific application. For example, for the fragmentation of ureteral, kidney or gall stones, a pulse width of about 10 to 1000 nanoseconds may be desirable.

While laser energy from two laser sources can be delivered through two independent optical fibers as known in the art, it would be beneficial to provide such an improved laser energy delivery system which could deliver such substantial laser energy through a single optical fiber or a bundle of optical fibers, a single hollow waveguide or an articulated arm. Such a system could also operate with two or more different laser types for subjecting the tissue sequentially to laser energy of different wavelengths to produce different effects on the tissue, such as cauterization by one wavelength, and cutting or ablation by another.

The present invention provides an improved laser energy delivery system which can accommodate designs having the above-discussed benefits and features.

SUMMARY OF THE INVENTION

The present invention provides a unique multiple laser system for subjecting a target site to laser energy of a relatively greater average power, and/or longer pulse width, or higher pulse repetition rate at the site, than is possible with a single laser.

The present invention is especially suitable for use in a medical system for delivering radiant laser energy pulses to a selected tissue site in a controlled manner. The invention is particularly well suited for use in surgical procedures for rapidly coagulating or cutting relatively soft tissues, as well as for ablating relatively hard tissues. Further, a plurality of different wavelengths of laser energy having different absorption characteristics can be delivered seriatim along a single axis directly or through one or more optical fibers or through an articulated arm to a target site.

In accordance with a preferred aspect of the invention, a laser device is provided for co-axial positioning of plural laser beams along a single axis. At least two laser resonators or oscillators are provided for producing a laser beam by each such resonator or oscillator. A rotary reflector means is positioned for intercepting at least one of the produced laser beams and for directing the intercepted laser beam separately from, but along a single axis defined by, the other laser beam.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

The present invention provides an improved laser delivery system which is especially suitable for use in surgery and other medical as well as industrial applications. The system includes plural laser resonators or oscillators which are uniquely arranged to emit beams of laser radiation seriatim along a single axis to a target site. The system can thus deliver laser energy at a higher average power and greater energy density, without damage to the transmitting waveguides, or at a relatively faster pulse repetition rate, to a tissue site or workpiece through a single waveguide, an articulated arm, a hollow waveguide or the like without requiring a change in the numerical aperture of the system.

While this invention is susceptible of embodiments in many different forms, this specification and the accompanying drawings disclose only some specific forms as examples of the invention. The invention is not intended to be limited to the embodiments so described, however. The scope of the invention is pointed out in the appended claims.

For ease of description, the laser device of this invention is described in a selected operating position, and terms such as upper, lower, horizontal, etc., are used with reference to this position. It will be understood, however, that the laser energy device of this invention may be manufactured, stored, transported, used, and sold in an orientation other than the position described.

Some of the figures illustrating embodiments of the apparatus show structural details and mechanical elements that will be recognized by one skilled in the art. However, the detailed descriptions of such elements are not necessary to an understanding of the invention, and accordingly, are not herein presented.

Further, the apparatus of this invention is used with, or incorporates, certain conventional components, the details of which are not fully illustrated or described in detail. For example, the apparatus of this invention may be employed with suitable conventional laser sources (laser resonators or oscillators), articulated arms, mirrors, hollow waveguides, optical fibers and coupling systems therefor, the details of which, although not fully illustrated or fully described, will be apparent to those having skill in the art and an understanding of the necessary functions of such components. The detailed descriptions of such components are not necessary to an understanding of the invention and are not herein presented because the structural and operational details of such components per se form no part of the present invention.

Figure 1:
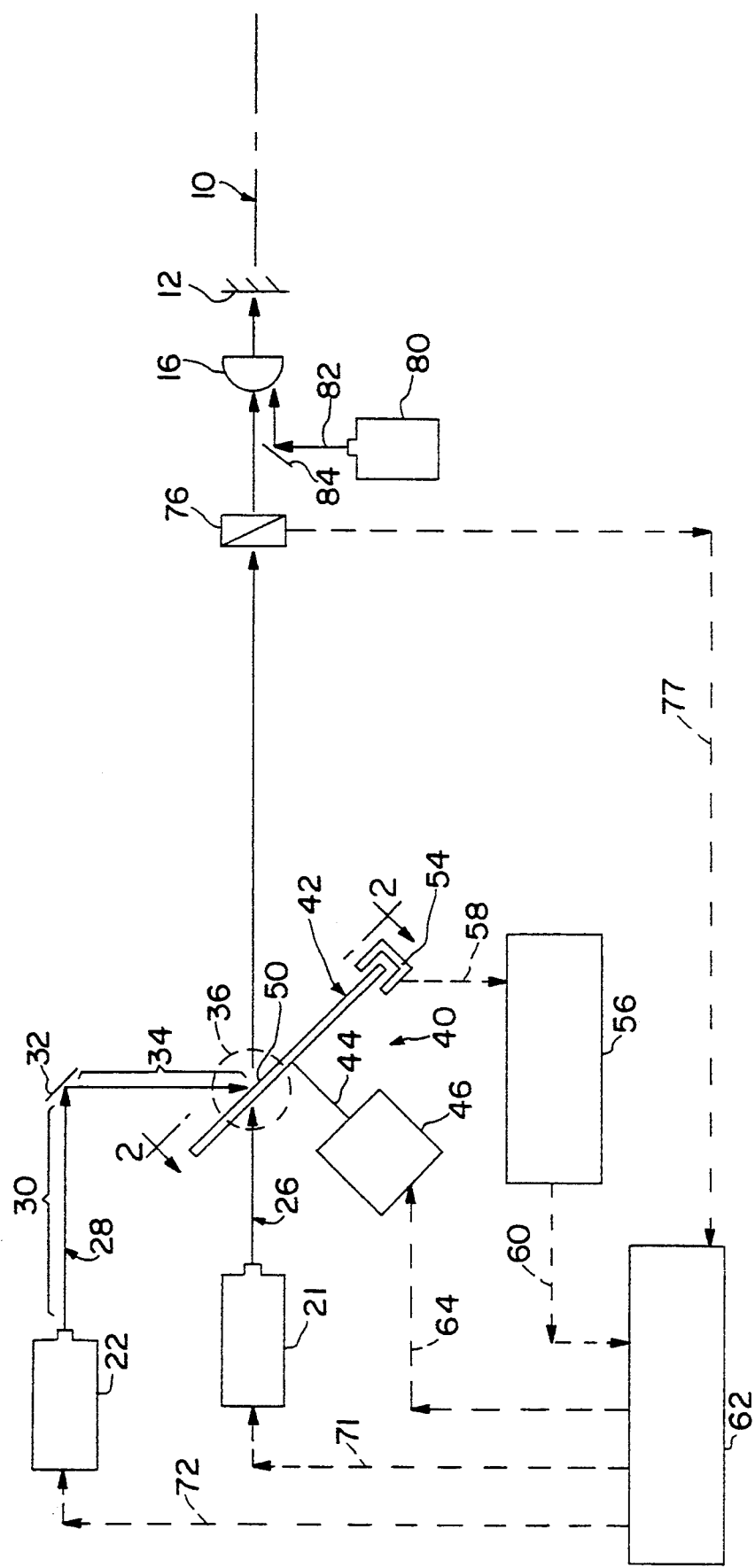
FIG. 1 is a schematic diagram of a plural head laser assembly of the present invention.
Figure 2:
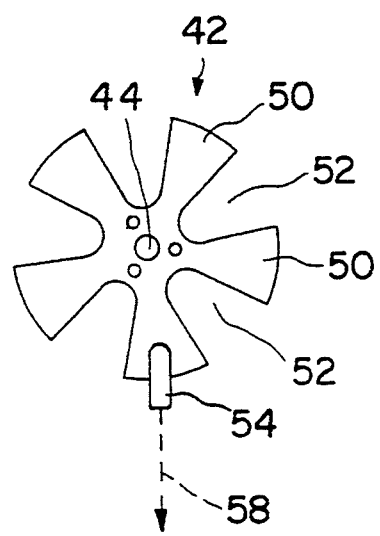
FIG. 2 is a partially diagrammatic view of the front of a rotary reflector taken generally along the plane 2—2 in FIG. 1.

A first type of laser device or system embodying the present invention is illustrated in FIGS. 1 and 2. The device is suitable for directing beams or pulses of laser radiation along a single axis 10 to a target or site 12. The system is particularly suitable for directing laser radiation to a target 12 of human tissue on the surface of a body, within a natural lumen or cavity, or in a surgically created area, cavity, or passage in body tissue. Typically, in surgical or other medical applications, the tissue at which the laser energy is directed may be characterized as defining a body site containing a material which is to be altered by the application of laser radiant energy. The material may be part of the tissue per se or may be an altered form of the tissue, such as cancerous tissue or atherosclerotic plaque. The material could also be an additional deposit on the tissue, or material to be removed for industrial purposes.

The laser radiation may be transmitted along the axis 10 to, and then through, a suitable optical fiber or like waveguide (not illustrated) as mentioned hereinabove, as desired. Such a waveguide can be a conventional, elongate, flexible, optical fiber which may assume a curved configuration and which functions as a laser energy-transmitting conduit. Such a fiber can be connected or coupled at its proximal end to a conventional lens or coupling assembly 16 into which the laser energy is directed from at least two laser sources or laser oscillators: a first laser oscillator 21 and a second laser oscillator 22. The waveguide can also be a hollow, flexible tube having a reflective inner lumen, such as is utilized for transmission of $CO_2$ laser energy.

The design, construction, and operation of laser oscillators, optical fibers, waveguides, laser reflecting mirrors, and coupling assemblies are well known in the art and are not described in detail herein. The details of the design, construction, and operation of such components .per se form no part of the present invention.

The terms "laser energy", "laser radiation", "laser beam," and variants thereof as used in this specification disclosure and in the claims will be understood to encompass pulsed wave or intermittent (chopped) continuous wave laser energy having a broad range of frequencies, pulse width and repetition rate characteristics, and energy densities or fluxes, and powers. The laser radiation may be suitably produced by a conventional laser device that generates pulses of the desired wavelength. Examples of laser types that can produce energies suitable for surgical applications include the following: excimer (e.g., 193 nanometers and 308 nanometers wavelength), alexandrite, titanium sapphire, argon, neodymium:yttrium aluminum garnet (Nd:YAG), frequency-doubled Nd:YAG (KTP laser), holmium:yttrium aluminum garnet (Holmium:YAG), erbium:yttrium aluminum garnet (Er:YAG), carbon dioxide ($CO_2$), ruby, alexandrite, and the like.

The laser oscillators 21 and 22 are arranged and controlled, in conjunction with other components, to produce separate, pulsed laser beams which are directed seriatim along the single axis 10. In the embodiment illustrated in FIG. 1, the two laser oscillators 21 and 22 are identical and are positioned so as to emit the pulsed laser beams from the emission ports in a substantially parallel configuration. The laser energy of the first laser oscillator 21 is transmitted in a pulsed beam 26 in a straight line which is coincident with, and which defines, the axis 10.

The second laser oscillator 22 produces a pulsed beam that travels along a first path 30 which is spaced from, but which is parallel to, the first laser oscillator beam 26. At the end of the first path 30, the second laser oscillator beam 28 is reflected by a reflector device, such as a conventional, laser energy-reflecting mirror 32 of a suitable type. The second beam 28 is reflected by the mirror 32 from the first path 30 along a second path 34 which is generally perpendicular to the first path 30 and which is thus also perpendicular to the first laser oscillator beam 26 on the axis 10. In operation, the mirror 32 is normally stationary. However, the mirror may include suitable, conventional means for adjusting the angle of the mirror relative to the first beam path 30 so as to facilitate alignment of the second beam path 34.

The second beam path 34 and the path of the first laser oscillator beam 26 intersect at a right angle generally at an intersection region 36. Although the paths of the beams are aligned to intersect in the region 36 (FIG. 1), the two laser oscillators are operated at different times, as will be described in detail hereinafter, so that the beam pulses do not coincide in time but only in space.

A reflector means 40 is provided at the path intersection region 36 for intercepting the second laser oscillator beam 28 and directing the beam along the axis 10. The reflector means 40 includes a rotary chopper means 42 mounted on a shaft 44 extending from a drive motor 46. The reflector means 40 may be a special or conventional light beam chopper. Choppers that are suitable for this application are commercially available under the designation Model 220 Light Beam Chopper from Ithaco, 735 West Clinton Street, P.O. Box 437, Ithaca, N.Y. 14851-6437.

With reference to FIG. 2, the rotary chopper means 42 includes a plurality of arms or blades 50. In the illustrated embodiment, five such blades 50 radiate outwardly and are equally spaced to define slots or voids 52. Each blade 50 has a front surface (i.e., the surface facing the incoming second laser oscillator beam 28) that is defined by a reflective surface, such as a coated glass mirror.

Preferably the motor 46 is an adjustable speed electric motor which is capable of rotating the chopper means 42 through a range of rotational speeds. For one presently contemplated mode of operation for the embodiment illustrated in FIGS. 1 and 2, the chopper means 42 can be rotated at a speed in the range of about 12 revolutions/minute to about 10,000 revolutions/minute.

A conventional reference pick up photosensor or position sensor 54 is located in a conventional manner adjacent the rotating member 42 for registering the presence or absence of a blade 50.

A conventional control system is provided and includes a revolution counter 56 for receiving a signal 58 from the position sensor 54. The revolution counter 56 registers the frequency or rate at which the blades 50 rotate past the sensor 54. A control signal 60 corresponding to this frequency is transmitted to a central processing unit 62. The chopper means motor 46 is preferably controlled through a conventional control signal 64 which can be responsive to the revolution counter signal 60 and a conventional frequency control system.

The first laser oscillator 21 is controlled from the central processing unit 62 via a control signal 71, and the second laser oscillator 22 is controlled from the central processing unit 62 through a control signal 72.

In operation, the central processing unit 62 alternately operates (i.e., actuates or fires) the first laser oscillator 21 and the second laser oscillator 22. For convenient operation, the motor 46 is typically operated at a constant, selected speed. When one of the five blades 50 is sensed by the position sensor (photosensor) 54, the slot or void 52 that is 180° away from the sensed blade 50 accommodates passage of the first laser oscillator beam 26 along the axis 10 to the target 12. The central processing unit 62 actuates the first laser oscillator 21 at this time to emit the laser energy beam or pulse 26. The pulse terminates by the time a blade 50 rotates into the beam path.

Figure 8:
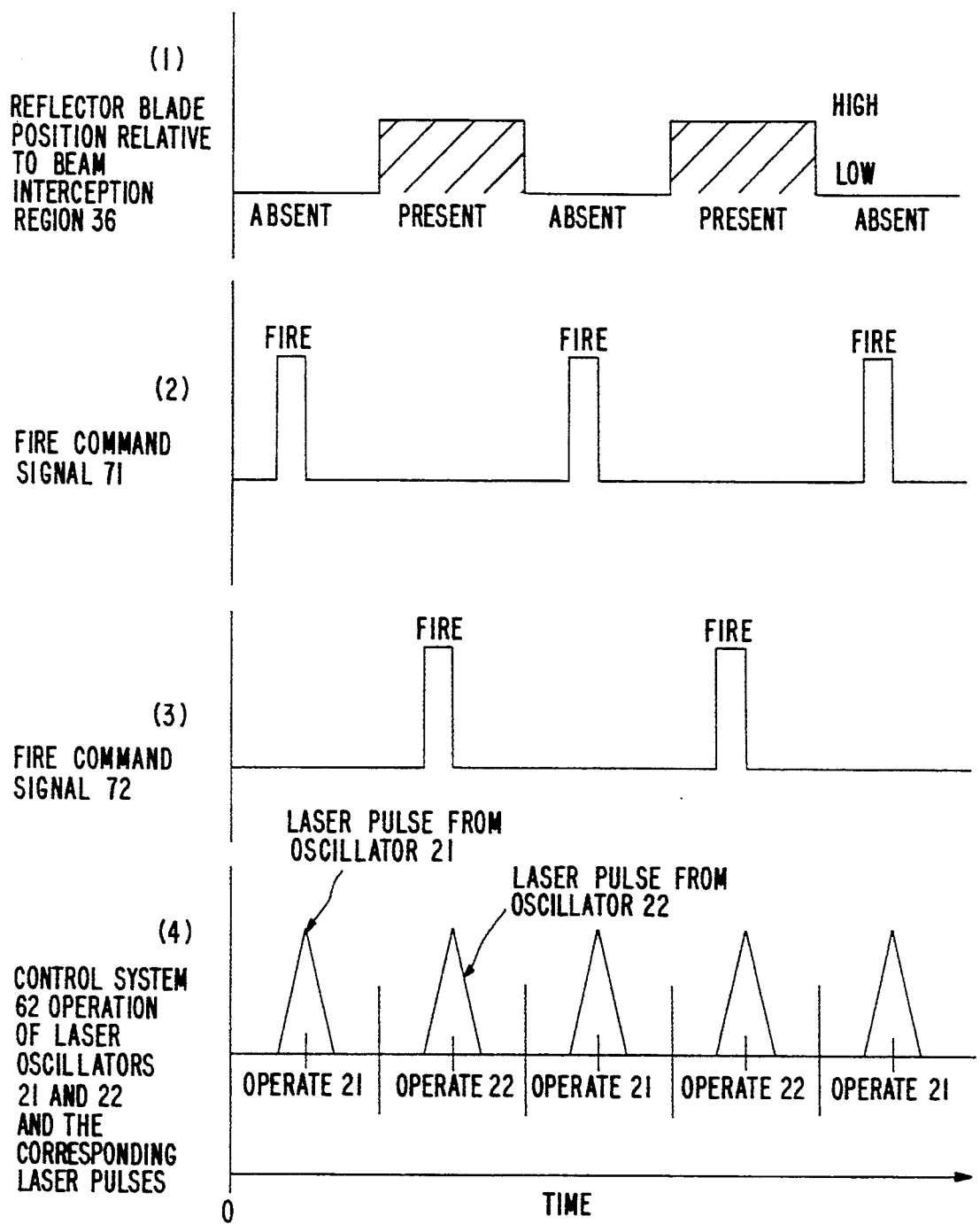
FIG. 8 is a simplified chart showing a graphical representation of the laser device system operation as a function of time.

When the rotating member 42 carries a blade 50 into the path of the beam 26 and, hence, also into the second laser oscillator beam path 34, the position of that blade 50 is determined by the position sensor 54 which senses the corresponding void or slot 52 which is 36° away. The central processing unit 62 then actuates the second laser oscillator 22 to emit a pulsed laser beam 28 which is reflected off mirror 32 as beam 34 which in turn is reflected off of the blade 50 of member 42 in the intercept region 36 and directed along the axis 10 to the target 12. This process is repeated as the reflecting member 42 rotates, and the laser beam pulses are thus transmitted alternately, and in a seriatim relationship, from the two laser oscillators to the target 12. This is graphically illustrated in FIG. 8 where the output signals of photosensor 54 are shown by waveform trace (1). "High" in the waveform (1) corresponds to the detection of the mirror parts of the rotary chopper means 42. "Low" in the waveform (1) corresponds to the detection of the open or aperture portions of rotary chopper 42. Waveform (2) of FIG. 8 shows the fire command signal 71 as issued by the central processing unit or controller 62. Waveform (3) of FIG. 8 shows the fire command signal 72 as issued by controller 62. The fire command signal 71 is issued to fire the oscillator 21 during the "low" portion of waveform (1) as shown in FIG. 8. This is the portion of time in which the laser pulse from oscillator 21 can propagate through to the coupling assembly 16 uninterrupted. The fire command signal 72 is issued only during the "high" portion of waveform (1), however. This is the portion of time in which a reflective blade 50 or the like is presented by the rotary chopper 42 in the path of a laser pulse from oscillator 22. This allows the pulse from oscillator 22 to be reflected by the reflective blade 50 at a coincidental intersecting point in space with the pulse from oscillator 21.

Thus the fire command signals 71 and 72 appearing in waveforms (2) and (3) of FIG. 8 respectively, are at least 180 degrees apart in phase. The mode of operation where two succeeding fire command signals are 180 degrees apart provides for the shortest possible interpulse delay, dictated by the angular velocity of the rotating member. This is useful in achieving twice the energy of a single pulse as far as photothermal ablation is concerned. As stated earlier, the interpulse delay is selected long enough to allow the acoustic effects of a first laser pulse to dissipate before a second laser pulse is introduced. In this manner of operation, the acoustic pulses from two succeeding laser pulses are not additive.

In another mode of operation, where a high repetition rate is desired, the two laser oscillators 21 and 22 are caused to fire with a relatively longer delay between their two corresponding pulses. For example, if a repetition rate of 50 pulses per second is desired, the laser oscillator 21 fires a pulse through an open part, at a repetition rate of 25 pulses per second, and approximately 20 milliseconds later, laser oscillator 22 fires a pulse, at a repetition rate of 25 pulses per second, into a mirror part. In this manner, the pulses are equally spaced from one another and a total of 50 pulses per second is achieved.

In any given instance, the pulse width must not exceed the time period that either the aperture or the beam reflecting surface is available to transmit or reflect the entire beam.

In one presently contemplated mode of operation, wherein a conventional five blade reflecting member 42 is employed, the laser oscillators 21 and 22 both can be holmium:YAG lasers that are each operable at least at about a 1-Hertz pulse repetition rate with a 10 to 10,000 microsecond typical pulse width (at a power output of about 8,000 milliJoules per pulse and at a wavelength of about 2,100 nanometers when operating at a maximum average power per oscillator of about 75 watts).

In general, as a trailing edge of a blade moves out of the path of the first laser oscillator beam 26 to permit the first beam 26 to pass to the target, a 800 microsecond margin time delay is preferably provided by the central processing unit 62 to insure that the first laser oscillator 21 is actuated when the beam path is completely open. Similarly, when the leading edge of the next blade 50 begins to move into the path defined by beam 34 for the second laser oscillator beam 28, an 800 microsecond time delay margin is provided by the central processing unit 62 before the second laser oscillator 22 is actuated. This insures that the entire beam 28 will be reflected by the reflecting blade 50. Of course this delay period is dependent upon the angular velocity of the blade.

The spacing of individual pulses can be utilized to modulate the acoustic effects of the applied, pulsed laser beam. In order to maximize the available acoustic effects, for example, for fragmenting a relatively hard material such as a urinary or biliary stone, the pulse spacing is minimized, i.e., the pulses are generated relatively close to one another. By spacing the consecutive pulses relatively close to one another, the pulse width is substantially increased, thus enabling a relatively higher average power to be delivered to a target without damage to the optical fiber used to transmit the same. This is particularly beneficial for the delivery of relatively high energy pulses from excimer lasers.

On the other hand, to minimize the acoustic effects, the individual pulses are spaced by at least 800 microseconds.

To maximize the thermal effects while minimizing the acoustic effects, the individual consecutive pulses are spaced by at least 800 microseconds but are cascaded within a time period that is less than the time period during which the heat generated by the preceding pulse is substantially dissipated. The duration of this latter time period varies with the type of tissue to be cut or ablated and is a function of the temperature integration time constant for the particular tissue. For example, when the thermal diffusion time constant k value is 150 milliseconds, utilization of the aforestated formula $$T_t = T_o e^{-t/k}$$

reveals that starting with a tissue temperature of 100° C. the tissue temperature after 5 milliseconds is $$T_t = 100 \times e^{-0.005/0.15} = 96.7°\ C.$$

Accordingly, the delivery of a second laser energy pulse within 5 milliseconds from the delivery of the preceding pulse will cause an accumulation of the respective thermal effects.

The present invention permits employment of commercially available medical lasers that produce laser beam energies subject to significant attenuation during transmission. In one mode of operation contemplated by the present invention, two such identical, conventional, medical lasers can be employed for the laser oscillators 21 and 22, and each oscillator is operated to produce laser radiation, for example, with a power of about 75 watts at the emission port so as to deliver about 65 watts to the target. The two laser oscillators can be operated to produce the pulses at a frequency of about 15 Hertz so that one pulse from one laser oscillator and the next pulse from the other laser oscillator occur sequentially and co-axially in a relatively short time span. This subjects the target to a total of 130 watts of average power, at a repetition rate of 30 pulses per second.

Preferably, the target 12, such as tissue, can be more efficiently cut by the laser beam pulses if the two pulses are transmitted to the tissue with a relatively short time interval between the two pulses. For example, for pulses each having a pulse width of about 250 microseconds and a repetition rate of 15 Hertz, it would be desirable to initiate the second pulse within 0.25 to 5 milliseconds of the end of the first pulse. By appropriate selection of the configuration of the rotary reflector or chopper (i.e., the number of reflecting surfaces and number of voids) and by appropriate selection of the rotational speed, pairs of consecutive laser beam pulses can be produced such that the time period between the two pulses is as small as a few hundred microseconds. The delivery of successive pulses with a relatively short time interval therebetween has the same thermal effect vis-a-vis the tissue target site in a thermodynamic sense as if it were a single pulse having the combined energies of the plural pulses. From an acoustic sense, however, the delivered pulses remain as two separate pulses inasmuch as acoustic shock and the generated vapor bubble dissipate within about 800 to 900 microseconds. That is, the emission of consecutive laser energy pulses can be controlled so that such pulses are emitted sufficiently close in time to one another to elicit an additive acoustic effect at a target site, e.g., kidney or gall stones. Similarly, two consecutive laser energy pulses can be emitted spaced in time from one another to elicit an additive thermal effect but without eliciting an additive acoustic effect at a target site, e.g., on a knee cartilage or at a blood vessel obstruction.

If desired, a detector 76 may be provided on the axis 10 downstream of the rotary reflector means 40 to monitor the energy levels of the beams. The detector 76 can be connected to supply a signal 77 to the central processing unit 62. The detector 76 may be of any suitable special or conventional design well known to those of skill in the art. The detailed design, construction, and operation of such a detector forms no part of the present invention.

An aiming beam may also be provided if desired. To this end, a helium-neon (HeNe) laser 80 may be provided for directing a beam 82 to a mirror 84 which reflects the beam 82 through the focusing lens 16 (when used). The helium-neon laser may be of the conventional type which, as known in the art, provides a low power aiming beam. The detailed design, construction, and operation of such an aiming beam laser forms no part of the present invention.

The system illustrated in FIG. 1 may also include additional components, such as other mirrors, coatings, focusing elements, housings, automatically-operated beam blocking devices or shutters, and the like (not illustrated). The detailed design, construction, and operation of such components per se form no part of the present invention.

It will also be appreciated that modifications may be made to the system illustrated in FIG. 1. For example, the second laser oscillator 22 need not be oriented to emit the beam 28 along a first path 30 which is parallel to the first laser oscillator beam 26. Instead, the mirror 32 could be eliminated and the second laser oscillator 22 could be oriented so as to initially emit its beam 28 directly along the beam path 34 in the direction generally perpendicular to the first laser oscillator beam 26.

The second laser oscillator 22 could also be oriented at other oblique angles, depending upon the orientation of the mirror 32 and rotary reflector means 40.

Various modifications or alternatives may be employed with respect to the design and operation of the rotary reflector means 40. For example, the rotary reflecting member 42 may be provided in the form of a disk with individual posts or apertures (not illustrated), rather than with blades 50 and slots 52 as illustrated in FIG. 2. Moreover, the laser oscillators can be Q-switched or mode locked in a known manner to produce relatively short pulses in synchronism with the rotary reflector means and at a repetition rate in the nanosecond, or picosecond, range so as to produce a greater acoustic effect and be suitable for fragmentation of kidney stones, gall stones, and the like.

Figure 3:
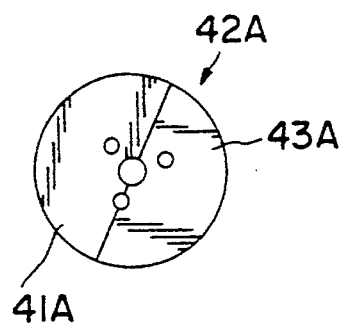
FIG. 3 is a view similar to FIG. 2 but showing an alternate embodiment of a rotary reflector.

A modification of a rotary reflecting member is illustrated in FIG. 3 wherein it is designated generally by the reference numeral 42A. The rotary reflecting member 42A is adapted to be rotated on a shaft in the same manner as the blade reflecting member 42 described above with reference to FIG. 2. However, the reflecting member 42A does not include separate blades per se. Rather, the member 42A has the form of a single disk provided with a transparent region 41A and a coplanar reflecting region 43A. Each region 41A and 43A has a substantially semicircular shape. The transparent region is preferably coated with an anti-reflection coating, and the reflecting region 43A is preferably coated with a dielectric reflective coating, as known in the art.

The single rotating disk 42A illustrated in FIG. 3 could also be modified by providing a number of pie-shaped transparent segments separated by pie-shaped reflecting segments (not shown).

Figure 4:
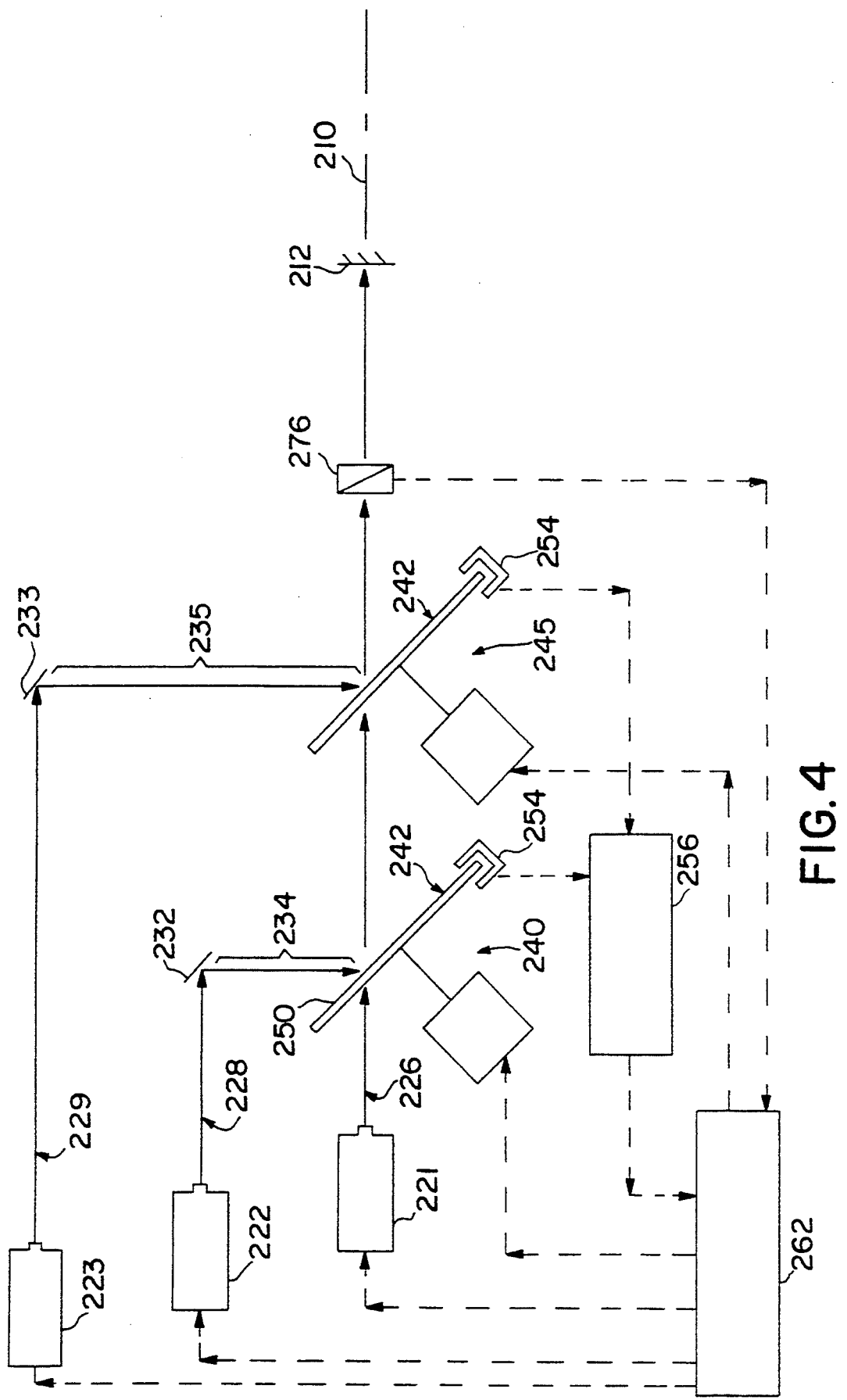
FIG. 4 is a schematic diagram of another embodiment of a laser device of the present invention.

The principles of the present invention can also be applied to systems employing more than two laser oscillators. FIG. 4 illustrates a system in which three laser oscillators are employed: a first laser oscillator 221, a second laser oscillator 222, and a third laser oscillator 223. The first laser oscillator is oriented to emit a pulsed laser beam 226 along an axis 210 which passes through a site or target 212. The second laser oscillator 222 is oriented to emit a beam 228 to a mirror 232 for reflection along a path 234 which intersects the path of the beam 226 along the axis 210. Similarly, the third laser oscillator 223 emits a beam 229 for reflecting off of a mirror 233 along a path 235 to intersect the path of the beam 226 (along the axis 210) at a right angle.

Figure 5:
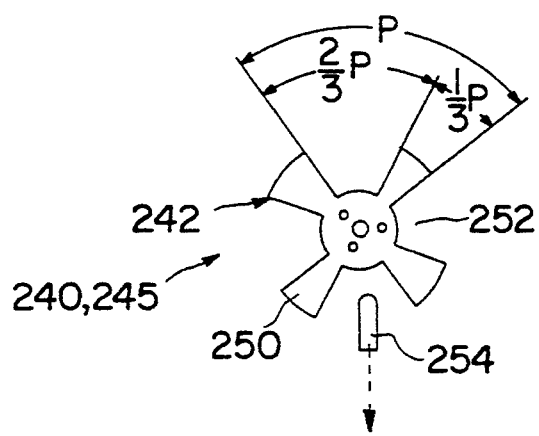
FIG. 5 is a plan view of a rotary reflector shown in FIG. 4.

A first rotary reflector means or chopper 240 is disposed at the intersection region of the paths of the beams 226 and 228, and a second rotary reflector means or chopper 245 is disposed at the intersection of the paths of the beams 226 and 235. Each chopper 240 and 245 includes a reflecting member 242 (FIG. 5) which includes four blades 250. The angular measurement or peripheral distance between the leading edge of one blade 250 and the leading edge of the next adjacent blade 250 is designated by reference letter P. The angular measurement of each blade 250 is $\frac{1}{3}$ P, and the angular measurement of the space between adjacent blades 250 is $\frac{2}{3}$ P.

As in the first embodiment illustrated in FIG. 1, a control system is provided for controlling the operation of the laser oscillators and rotary reflector choppers 240 and 245. Control signals are generally illustrated schematically by dashed lines in FIG. 4.

Each rotary reflector chopper 240 and 245 is operated in conjunction with position sensors 254 and a control system that includes a revolution counter 256 and central processing unit 262. The control system operates the first laser oscillator 221 to emit the first beam 226 between the blades 250 in both rotary reflector choppers 240 and 245. As the rotary reflector choppers 240 and 245 rotate, the generation of the laser beam pulse from the first laser oscillator 221 is terminated, and the second laser oscillator 222 is operated to generate the second laser beam pulse 228 which is reflected off of blade 250 which has now been rotated into the beam path interception region. The rotary reflector choppers 240 and 245 are regulated so as to rotate at a phase difference equal to the angular measurement of one of the blades 250. The rotary reflector means 245 lags the rotary reflector choppers 240 by an angle equivalent to $\frac{1}{3}$ P. Thus, when the reflector chopper 240 has rotated a blade to reflect the second beam 228, the reflector means 245 still presents a void or slot 252 at the beam path along the axis 210.

Upon further rotation of the reflector choppers 240 and 245, the reflector chopper 245 presents a blade 250 to reflect the third beam 229 which is emitted by the third laser oscillator 223 in response to control by the central processing unit 262.

A laser energy detector 276 may be provided in the path of the beams for monitoring the energy level and/or providing a feedback signal to the central processing unit for control of the laser oscillator power.

It will be appreciated that the system illustrated in FIG. 4 can be operated to provide a series of three laser pulses consecutively from three separate laser oscillators in a relatively short time span. While in the system illustrated in FIG. 4 two of the three provided laser oscillators interact with the rotary reflector means constituted by reflector choppers 240 and 245, the principles of the system illustrated in FIG. 4 may also be employed with four or more laser oscillators by altering the spacings of the chopper reflector surfaces or blades and making appropriate modifications to the control system.

Figure 7:
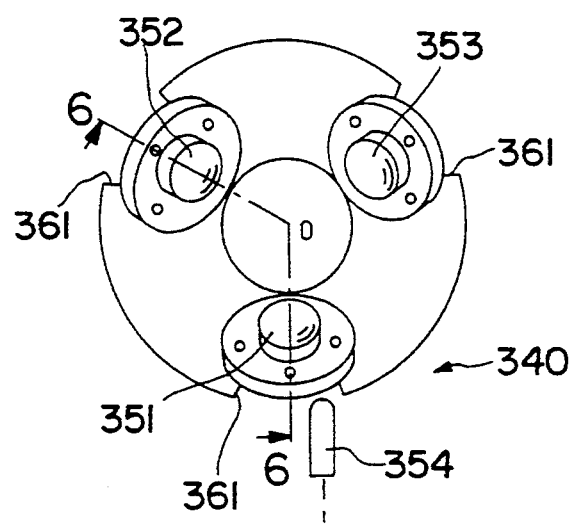
FIG. 7 is a view of a rotary reflector taken generally along the plane 7—7 in FIG. 6.
Figure 6:
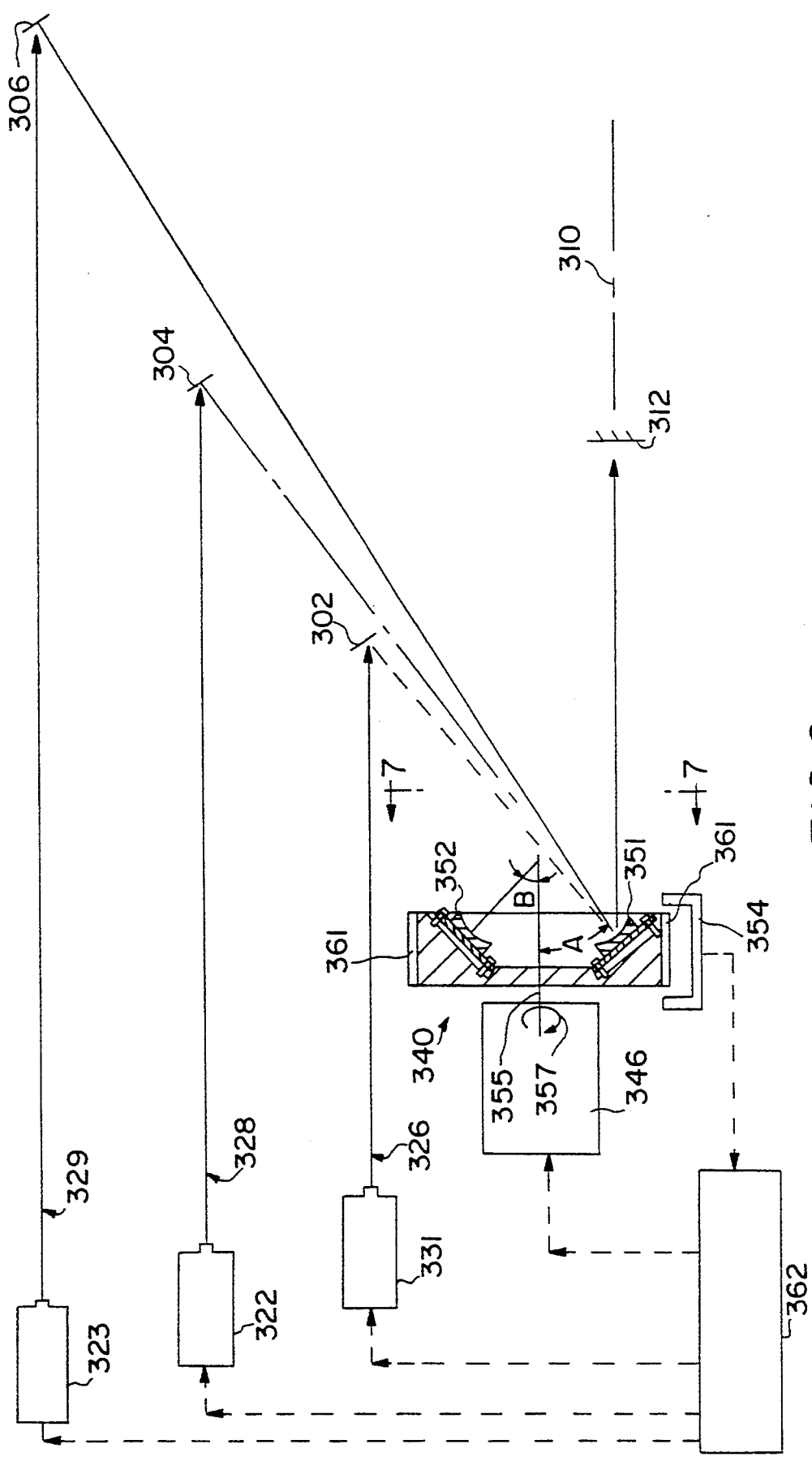
FIG. 6 is a schematic diagram of a further embodiment of a laser device of the present invention.

FIG. 6 illustrates yet another embodiment of the present invention which employs a first laser oscillator 331, a second laser oscillator 332, and a third laser oscillator 333, each interacting with a rotary reflector means. To that end, rotary reflector means 340 is provided to direct the beams from the individual laser oscillators along a common axis 310 to a target 312. As shown in FIG. 7, the reflector means 340 includes three mirrors 351, 352, and 353. The mirrors 351, 352, and 353 are mounted at oblique angles as shown in detail for mirrors 351 and 352 in a portion of FIG. 6 which includes a cross-sectional view taken along two planes 6—6 in FIG. 7. The reflector means 340 is rotated by a motor 346 about a central axis 355 in the direction of the arrow 357.

The rotary reflector means 340 is positioned to receive a first laser beam pulse 326 emitted from the first laser oscillator 331 and reflected to the reflector means 340 by a mirror 302, a second laser beam pulse 328 emitted from the second laser oscillator 332 and reflected to the reflector means 340 by a mirror 304, and a third laser beam pulse 329 emitted from the third laser oscillator 333 and reflected to the reflector means 340 by a mirror 306.

The three beams 326, 328, and 329 are directed to a common point into which each mirror 351, 352, and 353 is carried as the reflector means 340 rotates. The three reflecting mirrors 351, 352, and 353 each define a concave mirror surface. Each mirror 351, 352, and 353 is disposed at a different angle relative to the central axis 355 about which the rotary reflector means 340 rotates. As illustrated in FIG. 6, the mirror 351 is oriented at an angle A, and the mirror 352 is oriented at a greater angle B. The angle of orientation of the mirror 353 is not represented in the figures but is greater than the angle B.

The mirror angle A is selected so that the mirror 351, when located in the illustrated position, can reflect the laser beam 329 along the axis 310 to the target 312. The angle B of the mirror 352 is selected so that when the mirror 352 is rotated to the beam interception position (the position shown occupied by mirror 351 in the FIGURES), the mirror 352 will reflect the laser beam 328 from the second laser oscillator 332 along the same axis 310 to the target 312. Finally, the orientation angle for the mirror 353 is selected so that when the mirror 353 is in the beam interception position (the position shown occupied by mirror 351 in the figures), the mirror 353 will reflect the beam 326 from the first laser oscillator 331 along the axis 310 to the target 312.

A position sensor 354 is provided adjacent the rotating reflector means 340 for detecting spaced reference notches 361 which are each associated with one of the mirrors 351, 352, and 353. A controller 362, which can include a conventional central processing unit and counter responsive to the position sensor 354, is employed to control the rotational speed of the rotary reflector means 340 and the operation of the laser oscillators 331, 332, and 333. Control signal paths are generally illustrated schematically by dashed lines in FIG. 6.

In particular, as each mirror 351, 352, and 353 is rotated into the beam interception position, the controller 362 operates the laser oscillator associated with that mirror for generating a laser beam pulse. The generated beam pulses from the three lasers are produced seriatim and reflected seriatim to the target 312 so as to efficiently provide the pulses of laser energy in a relatively short time span.

Of course, more than three laser oscillators may be employed by adding additional mirrors to the rotary reflector means 340 and modifying the control system as necessary.

Further, it will be realized that the laser oscillators need not be positioned as shown to transmit the laser beams along the paths defined by the stationary mirrors 302, 304, and 306. If desired, the laser oscillators could be positioned to emit the laser beams along straight line paths directly to the rotating mirror interception point. However, the use of mirrors 302, 304, and 306 as illustrated accommodates alignment procedures by requiring merely the adjustment of relatively small mirrors rather than the special positioning of each entire laser oscillator.

Other modifications of the illustrated embodiments of the present invention may be made. It will be appreciated, however, that the present invention provides a novel means for directing laser beam pulses from a plurality of laser oscillators seriatim along a common axis. This system permits a number of pulses of laser energy to be directed to a target in a relatively short time period so as to efficiently cut or ablate tissues of different hardness. Further, the system accommodates the exposure of a target to a number of different types of laser energy from different types of laser oscillators where such a mode of operation is desired.

It will be readily apparent from the foregoing detailed description of the invention and from the illustrations thereof that numerous variations and modifications may be effected without departing from the true spirit and scope of the novel concepts or principles of this invention.

We claim:

1. A laser device for co-axial positioning of plural laser beams along a single axis, which device comprises:
   at least two laser oscillators for producing a laser beam by each oscillator;
   rotary reflector means positioned for intercepting at least one of said produced laser beams and directing the intercepted laser beam separately from, but along a single axis defined by, the other laser beam;
   alignment means for aligning the respective laser beams of each said oscillator at an angle along paths which intersect at a region;
   said reflector means includes a reflecting member rotation means for rotating said reflecting member through said path intersection region; and
   said device includes control means for operating one of said oscillators to emit a pulse of said one laser beam only as said reflecting member rotates through said path intersection region so as to reflect said one beam pulse along said single axis and for operating another of said oscillators to emit a pulse of said other laser beam only when said reflecting member has rotated beyond said path intersection region so that said other beam pulse passes unobstructed along said single axis.

2. The laser device in accordance with claim 1 wherein said rotary reflector means is a single rotary disk provided with plural, independent, reflecting surfaces and an equal number of separate apertures of substantially same size.

3. The laser device in accordance with claim 2 wherein a focusing element is present along the single axis to receive each laser beam reflected by said independent reflecting surface.

4. The laser device in accordance with claim 1 wherein said rotary reflector means is a single rotating disk provided with plural apertures in a continuous planar, reflecting surface.

5. The laser device in accordance with claim 1 wherein said rotary reflector means is a single (rotating disk provided with a transparent region and a coplanar reflecting region.

6. The laser device in accordance with claim 1 wherein said laser oscillators are Q-switchable in synchronism with said rotary reflector means.

7. The laser device in accordance with claim 1 wherein said rotary reflector means is rotatable at a speed in the range of about 12 revolutions per minute to about 10,000 revolutions per minute.

8. The laser device in accordance with claim 1 where in a pair of laser oscillators is provided and wherein said rotary reflector means is positioned to intercept periodically one of the produced laser beams.

9. The laser device in accordance with claim 1 wherein three laser oscillators interact with said rotary reflector means.

10. The laser device in accordance with claim 1 wherein three laser oscillators are provided and two of the three oscillators interact with said rotary reflector means.

11. The laser device in accordance with claim 1 wherein said laser oscillators emit holmium:YAG laser energy at a pulse rate of at least about 1 Hertz and having a pulse width in the range of about 10 to about 10,000 microseconds.

12. The laser device in accordance with claim 1 wherein said laser oscillators are mode-locked in synchronism with said rotary reflector means.

13. The laser device in accordance with claim 1 wherein said laser oscillators emit Nd:YAG laser energy.

14. The laser device in accordance with claim 1 wherein said laser oscillators emit excimer laser energy.

15. The laser device in accordance with claim 14 wherein the excimer laser energy is emitted at a wavelength of 193 nanometers.

16. The laser device in accordance with claim 14 wherein the excimer laser energy is emitted at a wavelength of 308 nanometers.

17. A laser device for co-axial positioning of plural laser beams along a single axis, which device comprises:
   at least two laser oscillators for producing a laser beam by each oscillator;
   rotary reflector means positioned for intercepting at least one of said produced laser beams and directing the intercepted laser beam separately from, but along a single axis defined by, the other laser beam; and
   control means for operating one of said oscillators to emit a pulse of said one laser beam only as a beam reflecting member rotates through a path interception region so as to reflect said one beam pulse along said single axis and for operating another of said oscillators to emit a pulse of said other laser beam only when said reflector means has rotated beyond said path interception region so that said other beam pulse passes unobstructed along said single axis.

18. The laser device in accordance with claim 17 wherein said control means causes two consecutive laser energy pulses to be emitted sufficiently close in time to one another to elicit additive acoustic effect at a target site.

19. The laser device in accordance with claim 17 wherein said control means causes two consecutive laser energy pulses to be spaced in time from one another to elicit an additive thermal effect without eliciting an additive acoustic effect at a target site.

* * * * *

REEXAMINATION CERTIFICATE (3092th)

United States Patent [19]
Saadatmanesh et al.

[11] B1 5,387,211
[45] Certificate Issued Dec. 31, 1996

[54] MULTI-HEAD LASER ASSEMBLY

[75] Inventors: Vahid Saadatmanesh, Irvine; Marvin P. Loeb, Huntington Beach, both of Calif.

[73] Assignee: Trimedyne, Inc., Irvine, Calif.

Reexamination Request:
No. 90/004,023, Oct. 30, 1995

Reexamination Certificate for:
Patent No.: 5,387,211
Issued: Feb. 7, 1995
Appl. No.: 28,839
Filed: Mar. 10, 1993

[51] Int. Cl.$^6$ .................................................. A61N 3/00
[52] U.S. Cl. ...................... 606/10; 606/12; 606/17; 607/89
[58] Field of Search ..................... 606/10–12, 17, 606/18; 607/88, 89; 359/196, 204, 212, 216, 220; 372/10, 15, 17, 23

[56] References Cited

U.S. PATENT DOCUMENTS 3,353,115  11/1967  Malman .
3,388,314  6/1968   Gould .
3,533,707  10/1970  Weiss .
3,543,183  11/1970  Heimann .
3,928,815  12/1975  Hellwarth .
5,387,211  2/1995   Saadatmanesh et al. .

OTHER PUBLICATIONS

R. W. Hellwarth, *Control of Fluorescent Pulsations*, Advances in Quantum Electronics, 1961.
R. W. Hellwarth, *Theory of the Pulsation of Fluorescent light from Ruby*, Physical Review Letters, vol. 6, No. 1, Jan. 1, 1961.
Theodore H. Maiman, *Optical Maser Action in Ruby*.
Jeff Hecht, *An Introduction to Laser History*, Laser Pioneer Interviews.
Robert J. Pressley, Ph.D., *Handbook of Lasers with Selected Data on Optical Technology*.

*Primary Examiner*—Angela D. Sykes

[57] ABSTRACT

A laser device is provided for the co-axial positioning of plural laser beams of same or different wavelengths along a single axis. At least two laser oscillators are provided, each producing a laser beam. A rotary reflector is positioned for intercepting at least one of the produced laser beams and directing the intercepted laser beam separately from, but along a single axis defined by another laser beam.

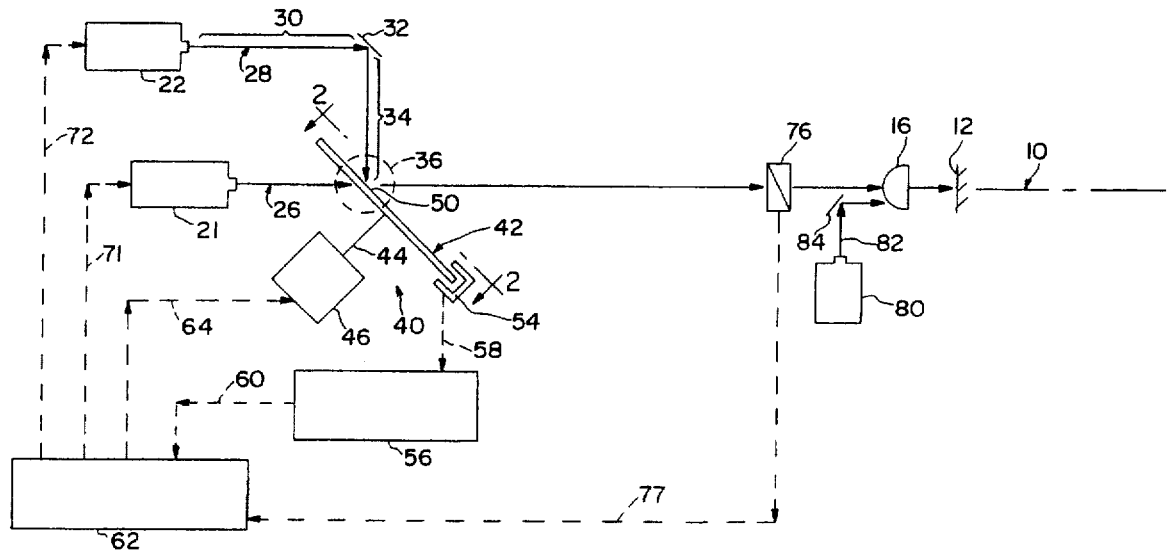

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *